(12) United States Patent
Hasumi et al.

(10) Patent No.: US 8,088,397 B2
(45) Date of Patent: Jan. 3, 2012

(54) HUMAN LYMPHOCYTE VACCINE ADJUVANT

(75) Inventors: Kenichiro Hasumi, Tokyo (JP); Dean LeMar Mann, Rockville, MD (US); Kim Graulich Hankey, Edgewood, MD (US); Kristina Michelle Holt, Annapolis, MD (US)

(73) Assignees: Hasumi, LLC, New York, NY (US); University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 12/824,577

(22) Filed: Jun. 28, 2010

(65) Prior Publication Data

US 2010/0266534 A1 Oct. 21, 2010

Related U.S. Application Data

(62) Division of application No. 10/783,259, filed on Feb. 20, 2004, now Pat. No. 7,745,157.

(51) Int. Cl.
*A61K 45/00* (2006.01)
*G01N 33/00* (2006.01)

(52) U.S. Cl. .................................. 424/278.1; 435/7.24

(58) Field of Classification Search ....................... None
See application file for complete search history.

*Primary Examiner* — Jeffrey S. Parkin
*Assistant Examiner* — Louise Humphrey
(74) *Attorney, Agent, or Firm* — Acker Wood IP Law, LLC; Gwen R. Acker Wood

(57) ABSTRACT

The present invention relates to an adjuvant derived from human lymphocytes. The adjuvant can be used in combination with traditional vaccines or cancer immunotherapy, to enhance the response of the patient's immune system to the vaccine or other immunotherapeutic agent. The adjuvant is derived from the supernatant collected from cultured activated lymphocytes.

12 Claims, 10 Drawing Sheets

HUMAN LYMPHOCYTE VACCINE ADJUVANT

CROSS-REFERENCE TO RELATED APPLICATIONS

This application claims priority under 35 USC 119(e) to provisional application Ser. No. 60/449,528, filed Feb. 21, 2003.

FIELD OF THE INVENTION

The present invention relates to an adjuvant derived from human lymphocytes. The adjuvant can be used in combination with traditional vaccines or cancer immunotherapy, to enhance the response of the patient's immune system to the vaccine or other immunotherapeutic agent.

BACKGROUND INFORMATION

Immunological adjuvants are used in combination with vaccines to augment the immune response to the antigen. One way in which immunological adjuvants function is by attracting macrophages to the antigen, so that the macrophages can present the antigen to the regional lymph nodes and initiate an effective antigenic response. Adjuvants may also act as carriers themselves for the antigen, or may influence the immune response by other mechanisms such as depot effect, cytokine induction, complement activation, recruiting of different cell populations of the immunological system, antigen delivery to different antigen presenting cells, regulation of the expression of HLA class I or class II molecules and the stimulation to produce different antibody subtypes. Many of the newer vaccines are only weakly immunogenic and thus require the presence of adjuvants.

Materials having adjuvant activity are well known. Alum $(Al(OH)_3)$, and similar aluminum gels are adjuvants licensed for human use. The adjuvant activity of alum was first discovered in 1926 by Glenny (Chemistry and Industry, Jun. 15, 1926; J. Path. Bacteriol, 34, 267). Aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and, more recently, a HBsAg vaccine has been adjuvanted with alum.

Other materials are also known to have adjuvant activity, and these include: Freund's complete adjuvant, a water-in-mineral-oil emulsion which contains killed, dried mycobacteria in the oil phase; Freund's incomplete adjuvant, a weaker formulation without the mycobacteria; saponin, a membrane active glucoside extracted from the tree Quillia saponaria; nonionic block copolymer surfactants, non-metabolised synthetic molecules which tend to bind proteins to cell surfaces; ISCOMS, lipid micelles incorporating Quil A (saponin) which mimic, in physical terms, infectious particles; and muramyl dipeptide, a leukocyte stimulatory molecule that is one of the active components of killed mycobacteria. A known adjuvant in cancer therapy is bacillus calmette guerin (BCG) which is used in combination with various anti-cancer vaccine strategies. GM-CSF has also been found to be an effective adjuvant when used in combination with autologous tumor cells.

With all of these agents, toxicity, unacceptable chronic reactions and/or low potency (in the case of BCG) are features which currently limit their use as potential adjuvants. Thus there is an ongoing and current need for new adjuvants to boost the human immune response to vaccines, in both cancer therapy and other disease treatments.

One line of research in the development of adjuvents has been directed to the study of dendritic cells. Dendritic cells (DC) are professional antigen presenting cells (APC) that have the unique capacity to initiate primary immune responses in vivo and in vitro (1-3). They are derived from myeloid (DC1) or lymphoid (DC2) precursors and are distributed in their immature form throughout the body in tissues that commonly encounter environmental pathogens (skin, mucus membranes, gut epithelia, etc.) (1,2,4-7). Whereas DC1 and DC2 comprise a small percentage of the total number of mononuclear cells in the peripheral circulation, DC1 precursors in the form of CD14+/CD11c+/HLA-DR+ monocytes are relatively abundant, constituting about 10% to 15% of mononuclear blood cells (11-15).

Immature DC express a host of surface structures that are involved in antigen acquisition, DC activation/maturation, and antigen presentation (1,2,8). Once DC encounter antigen, they undergo a maturation process characterized by the up-regulation of HLA class I and II molecules as well as co-stimulatory molecules and interact with cognate receptors on T and B lymphocytes, resulting in the generation of antigen specific cellular and humoral immune responses (1,2,9,10).

DC are considered to be the primary APC in the immune system. The ability to isolate these cells and/or their precursors and to study them in vitro has added considerable dimension to knowledge of their role in innate and acquired immunity (1,2). The classic means of generating human DC in vitro is to isolate and enrich CD14+-monocytes from peripheral blood and culture them for various periods of time in GM-CSF and IL-4 followed by final maturation with a number of cytokines, including IL-2, IL-6, IL-7, IL-13, IL-15, TNFα, IL-1β, (16,36) or with various other agents including lipopolysaccharides, $PGE_2$, type 1 interferons, or double-stranded RNA (20-24).

Numerous investigators have shown that these in vitro generated monocyte-derived DC are potent antigen presenting cells (APC) capable of initiating primary and recall antigen-specific CD4+ and CD8+ T cell responses (27-30). Recent in vitro studies have generated a rather extensive body of information regarding the biology of DC1 and shed light on the processes whereby antigen specific immune responses are generated in vivo (1-2). In the peripheral tissues, immature DC acquire antigenic materials in the context of danger signals initiating a complex cytokine/chemokine milieu that is generated by DC and other cell types in the vicinity (31). Soluble mediators produced by DC may act in an autocrine or paracrine fashion. T cells produce additional cytokines and chemokines following interaction with antigen armed DC, as do other immune cells that are activated by the cytokines released (32-35). This complex network of interactions may in turn create an environment that promotes the generation of DC from their monocyte precursors.

Several investigators have described the use of various cell-free culture supernatants, also referred to as "conditioned media" as DC maturation agents. These media contain more or less well defined mixtures of cytokines (12,25,26). Monocyte conditioned media (MCM), containing IFNα, IL-1β, IL-6, and TNFα, has been shown to induce expression of CD83 and p55, surface molecules that are characteristic of mature DC (26). However, when combinations of these cytokines were added to immature DC at concentrations comparable to those found in the conditioned media, they were less effective in maturing DC compared to MCM. These results suggest that additional components were required to affect full maturation of immature DC.

In one study, Kato et al prepared conditioned media (designated TCCM) by culturing isolated T cells with anti-CD3 monoclonal antibodies that had been adhered to plastic surfaces (25). This media was able to mature immature DC that had been generated from monocytes cultured in (GM-CSF and IL-4. Interestingly, different clones of anti-CD3 induced different quantities of soluble CD40 ligand and IFN (and these differences were reflected in the capacity of the media to mature DC.

Whereas MCM and TCCM are very effective mediators of final DC maturation, their capacity to differentiate monocytes into immature DC was not reported. The inventors are aware of one report where this activity was observed with media from PBMC stimulated with CpG-A oligonucleotides (33). It is well established that CpG-A induces type 1 interferons (IFN∀/IFNƎ) production by plasmacytoid DCs, a minor cellular component in PBMC (6, 37-39). In the cited study, antibodies to IFN∀ diminished but did not abrogate the activity of this culture media suggesting that additional cytokines might be participating in the induction of monocyte differentiation. This is certainly possible since IFN∀ is known to induce production of cytokines in other cell types (including T cells) that may affect monocyte differentiation (6,38,39).

It is thought that compounds or compositions which promote that maturation of dendritic cells, when administered in combination with a vaccine antigen, will result in more antigen presenting cells presenting the vaccine antigen to T lymphocytes and B cells, thus bolstering the immune response to the vaccine antigen.

SUMMARY OF THE INVENTION

The present invention solves the above need by providing new adjuvants, based on products of human lymphocytes, that provide immunological potentiation and increase the amount and quality of the immune response to vaccine antigens.

In one aspect of the invention, the adjuvant is derived from supernatant material collected from in-vitro stimulated cultured human peripheral blood mononuclear cells. Naïve T-cells are activated during the culture process. The adjuvant works to enhance the ability of a vaccine to initiate, create, boost and/or sustain an immune response to an agent in humans, and other animal or plant species.

The present invention provides an adjuvant based on a mixture of cytokines and chemokines obtained from peripheral blood mononuclear cells stimulated with antiCD3/CD28-coated beads. As used herein, the term "lymphocyte conditioned medium (LCM)", will be used to refer to this adjuvant. It has been found that LCM is a highly effective conditioned medium with the capacity to mature monocyte-derived DC and to render monocytes into potent APC. The adjuvant can provide a rapid, cost-effective, and probably more "physiologic" method to derive large amounts of DC1 from precursor cells in vitro, and LCM can therefore function as an effective vaccine adjuvant. It is thought that PBMC-derived products may provide the cytokine milieu required to rapidly generate DC1 from their precursors after the initiation of an immune response in vivo.

The cytokines and chemokines identified in the LCM preparations are known to participate in the generation of immune responses by their autocrine or paracrine effect on APC and responding T and B cells. The concentrations of cytokines found in the LCM are considerably lower than the concentrations of cytokines that are commonly used to differentiate monocytes into immature DC or to mature DC in vitro (16,22). LCM contains cytokines (IFN, IL-12) and soluble CD40 ligand that are known to polarize T cells towards a TH1 response as well as cytokines (IL-4 and IL-10) that polarize T cells towards the TH2 responses (5,40,41). These latter cytokines may also induce T cell anergy when present in cultures of antigen presenting immature DC and T cells. However, the presence of IL-10 and the small amounts of IL-4 in the LCM did not abrogate a T cell recall response to TT; rather, the T cell responses were augmented, clearly demonstrating that the effect of TH1 cytokines dominates.

In addition to proinflammatory cytokines, high concentrations of chemokines were detected in LCM. These chemokines are produced by lymphoid cells as well as by non-lymphoid cells in the context of an inflammatory process (35,42). As an example, RANTES is produced by CD8+-T cells and it in turn induces the generation of other cytokines and chemokines (MIP1Ǝ, IL-2, IL-6, and type 1 interferons) that activate T cells as well as monocytes (43). The induction of these cytokines and chemokines might be representative of what occurs when T cells are activated by APC in vivo in the context of antigen presentation. Following T cell activation through T cell receptor and CD28 ligation, the T cells release cytokines and chemokines that are known to influence the differentiation of monocytes into immature DC as well as their migration to regional lymphoid organs. These soluble factors may also attract DC precursors and other APC to the environment of initial antigen encounter (danger signal). Together the cytokines and chemokines produced by activated T cells and, downstream, by bystander cells could be expected to magnify the immune response cascade, a desirable property of an adjuvant. There is an increasing awareness of the capacity of various cytokines to act as adjuvants for vaccines, in particular GM-CSF and IL-2.

The generation of a PBMC-derived conditioned medium has the capacity to generate large amounts of immature DC from their precursors and to mature monocyte-derived DCs. This rapid and cost-effective method can play an important role in the development of future vaccines, and for use as an adjuvant. In addition, the wide range of cytokines and chemokines contained in LCM suggests a more physiologic stimulus, providing a cytokine milieu similar to what might be found in vivo once T cells encounter antigen.

The present invention provides a method of using the adjuvant, both supernatant and cell-based, in combination with a vaccine antigen, to provide an enhanced immune response to the vaccine.

It is an object of the present invention, therefore, to provide a vaccine adjuvant capable of enhancing immunogenic response to the vaccine.

It is a further object of the invention to provide a vaccine adjuvant derived from human lymphocytes.

It is a further object of the invention to provide a vaccine adjuvant derived from supernatant collected from stimulated cultured human lymphocytes.

It is an additional object of the invention to provide a method of using the vaccine adjuvant, by administering the adjuvant to a host animal in combination with a vaccine.

These and other objects of the invention will become more readily apparent from the following description, drawings, and appended claims.

Data represents means±SEM of 9 experiments. * indicates p<0.05, and ** indicates p<0.005.

Figure 2A:
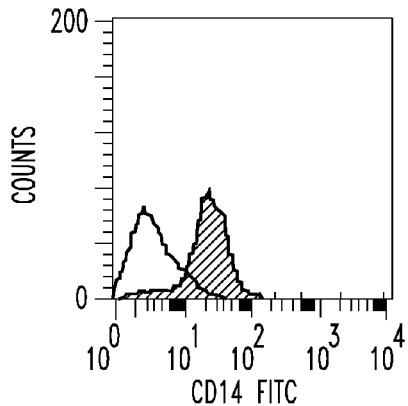
Figure 2B:
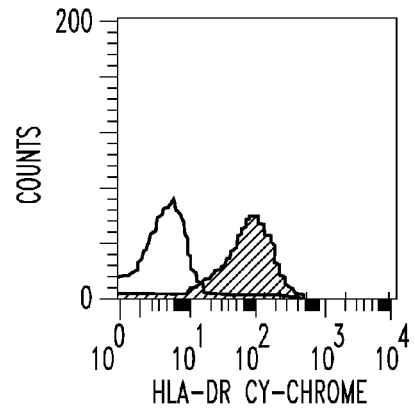
Figure 2C:
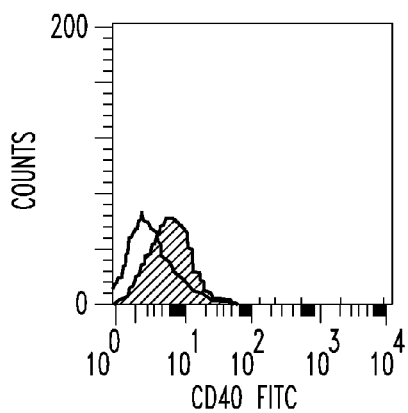
Figure 2D:
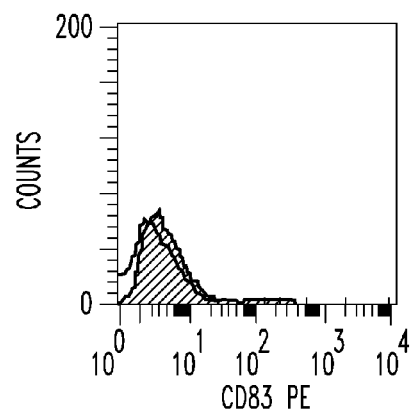
Figure 2E:
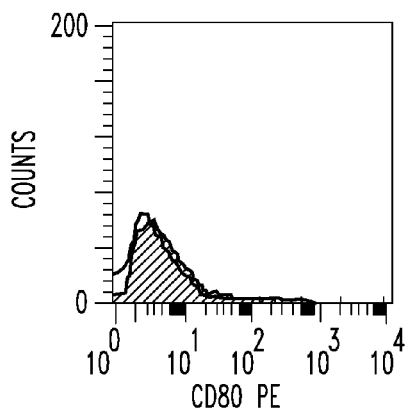
Figure 2F:
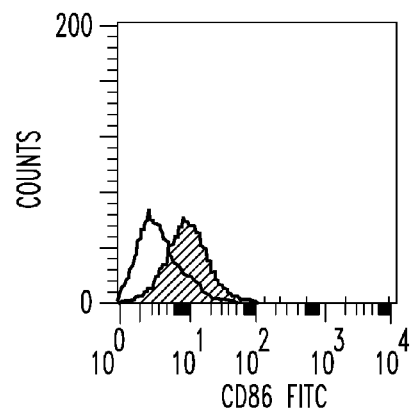
Figure 2G:
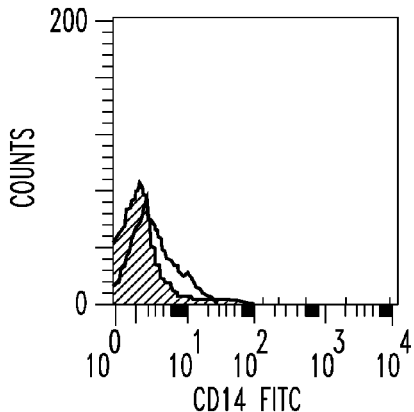
Figure 2H:
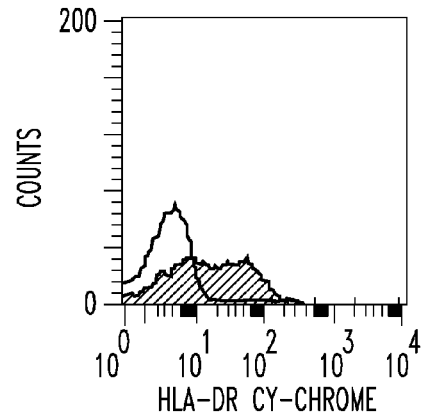
Figure 2I:
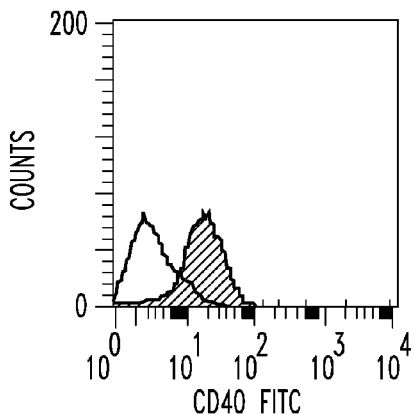
Figure 2J:
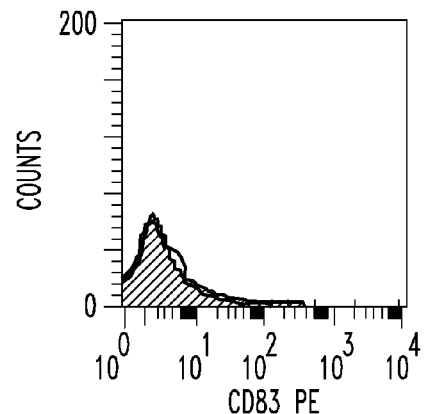
Figure 2K:
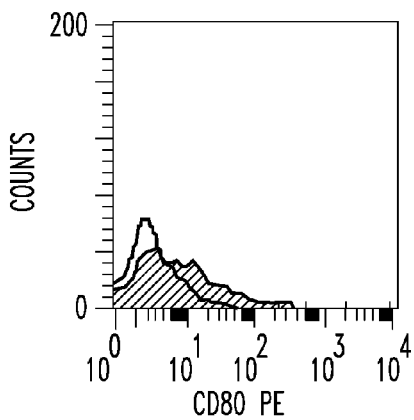
Figure 2L:
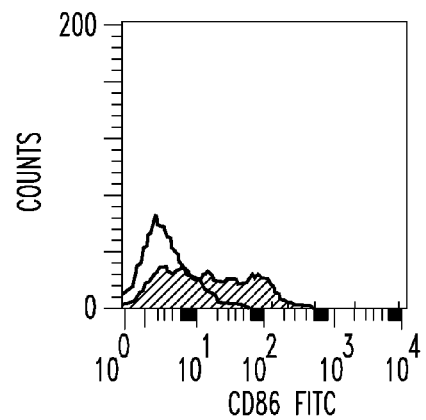
Figure 2M:
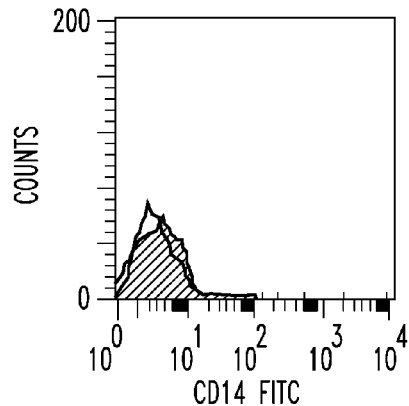
Figure 2N:
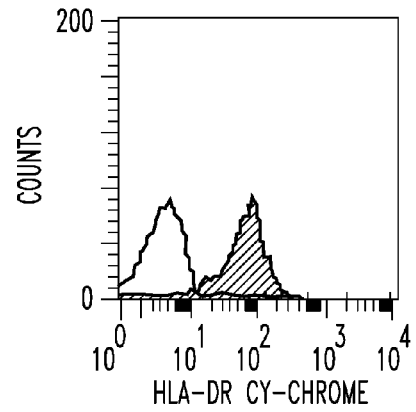
Figure 2O:
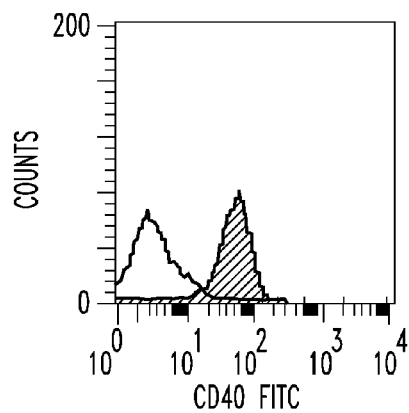
Figure 2P:
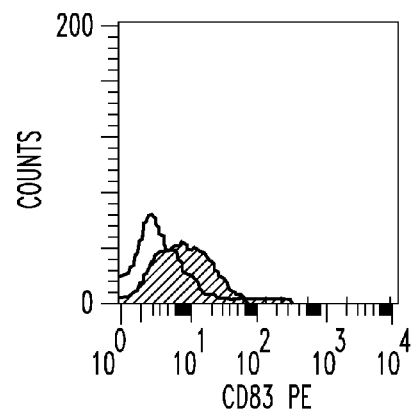
Figure 2Q:
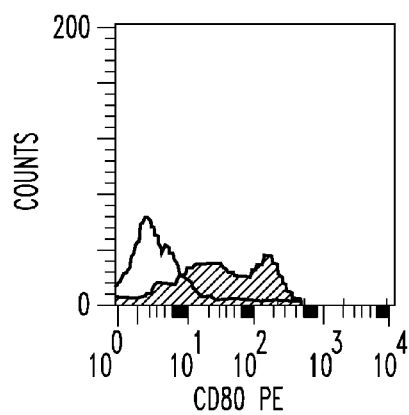
Figure 2R:
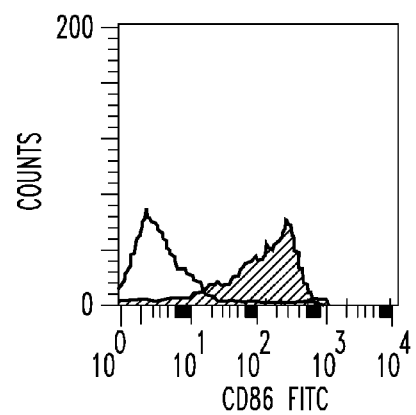
Figure 2S:
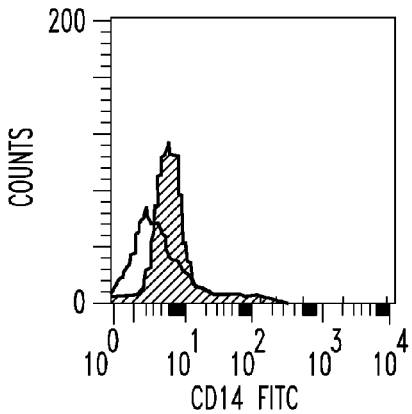
Figure 2T:
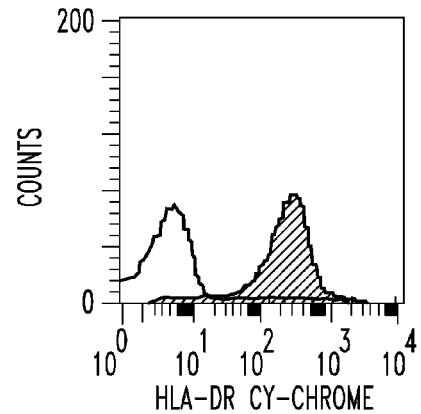
Figure 2U:
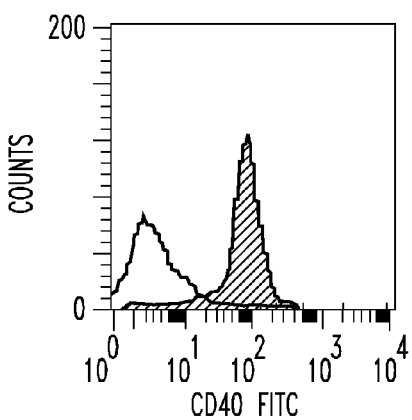
Figure 2V:
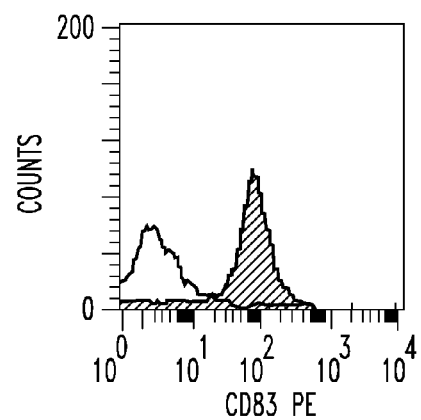
Figure 2W:
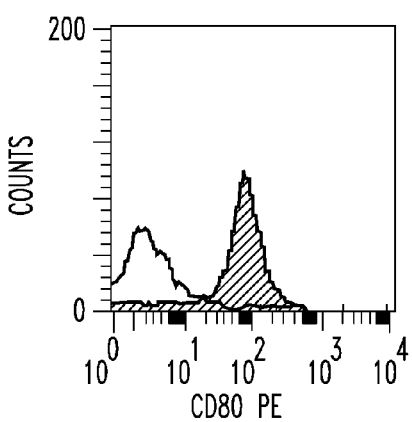
Figure 2X:
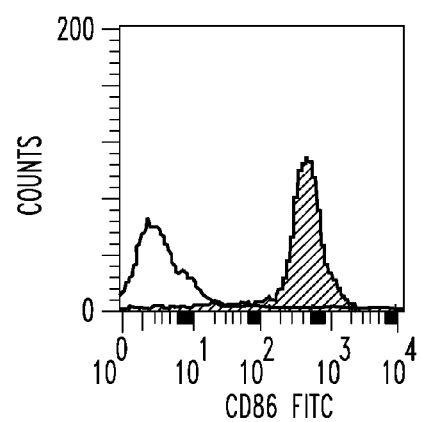

FIGS. 2A-2X: Effect of LCM on maturation of immature monocyte-derived DC. Elutriated monocytes were cultured with GM-CSF/IL-4 for 3-4 days followed by addition of media alone (FIGS. 2G-2L), LCM (FIGS. 2M-2R), or Maturation Cocktail (FIGS. 2S-2X) for 48 hours. Monocytes cultured in cRPMI only (FIGS. 2A-2F) were used as a negative control. CD11c$^+$– DCs were examined for surface expression of CD14, HLA-DR, CD40, CD83, CD80, and CD86 by flow cytometry. Open histograms represent staining of DC with isotype control mAb, and shaded histograms represent staining of DC with specific mAb.

FIGS. 3A-3E: LCM differentiates monocytes to a DC-like phenotype when added to whole populations of PBMC. CD11c+ cells were analyzed for expression of CD14 (FIG. 3A), HLA-DR (FIG. 3B), CD40 (FIG. 3C), CD80 (FIG. 3D), and CD86 (FIG. 3E) at 0, 3, and 5 day. Data represents the mean of two experiments.

Figure 4:
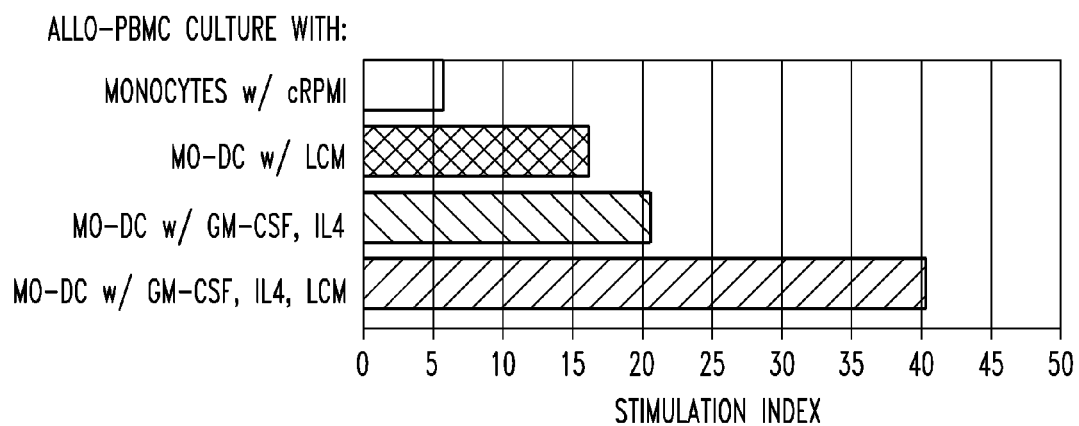

FIG. 4: DCs generated from elutriated monocytes cultured in the presence of LCM are superior in their ability to stimulate allogeneic PBMC responses than those cultured in the absence of LCM. Allogeneic PMBC ($1\times10^5$ cells) were cultured in 96-well U-bottom culture plates with $1\times10^4$ stimulator cells as indicated in triplicate. PBMC response is expressed as the Stimulation Index (ratio of the average CPM (counts per minute) of an individual MILR to the average CPM of PBMC cultured alone in control media).

Figure 5A:
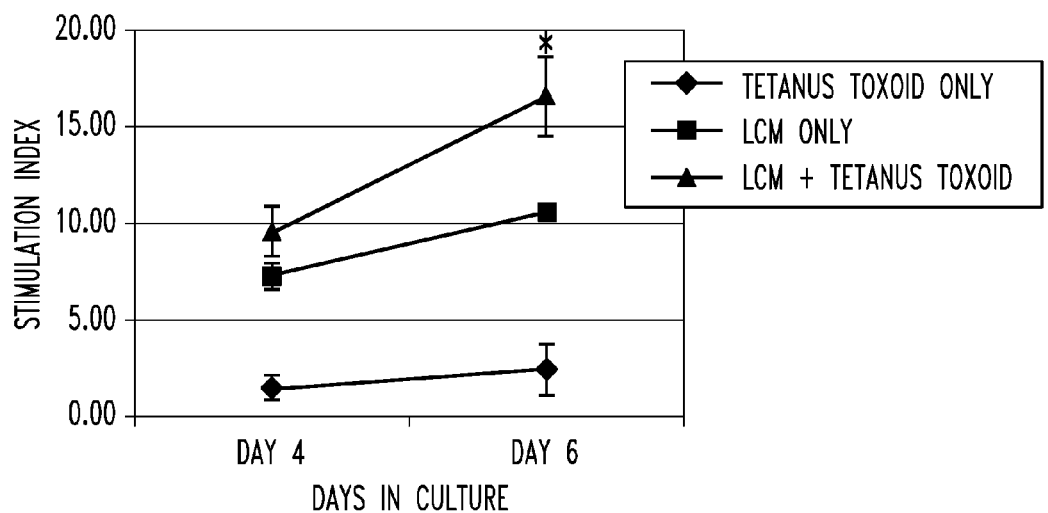
Figure 5B:
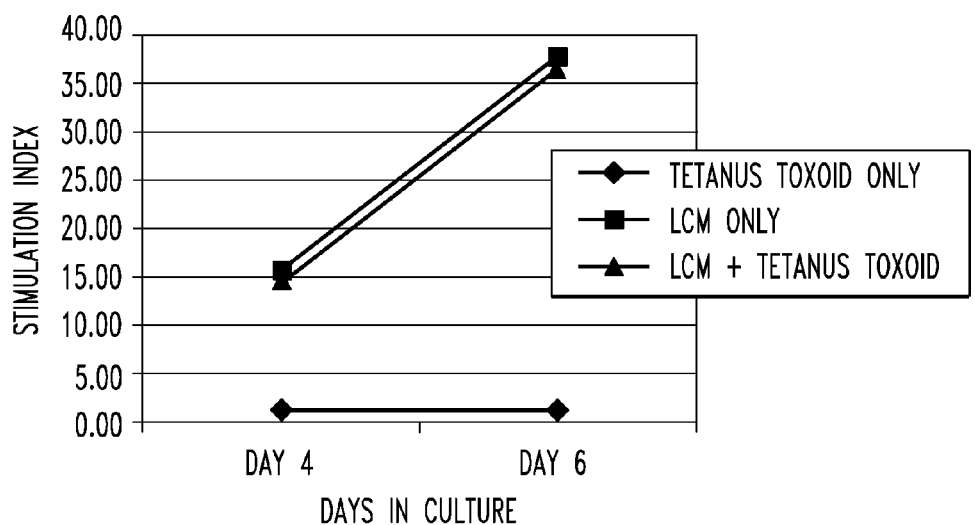

FIGS. 5A-5B: LCM augments the proliferative response of whole PBMC to tetanus toxoid. Whole PBMC or PBMC depleted of monocytes were cultured in 96-well U-bottom culture plates in LCM with or without 10:g/ml tetanus toxoid protein and in cRPMI with antigen. PBMC cultured in cRPMT containing 10:g/ml ConcanavilinA served as the positive control (data not shown). Response is expressed as the Stimulation Index (SI) (ratio of the average CPM of PBMC culture with TT, LCM, or both TT and LCM (FIG. 5A) to the average CPM of PBMC cultured alone in cRPM (FIG. 5B)). Data represents the mean of two experiments. * Indicates p<0.05.

DETAILED DESCRIPTION OF PREFERRED EMBODIMENTS

In one aspect, the present invention provides a method of enhancing the immune response to a vaccine antigen in a host mammal, comprising administering lymphocyte conditioned medium, the supernatant derived from activated human lymphocyte cells cultured with growth media, in combination with the vaccine antigen. Preferably, the mammal is a human. Culture methods and protocol are standard and known in the art. Human (or other mammal, depending on the mammal to be treated) peripheral blood mononuclear cells (PBMC) obtainable from any source are diluted in commercially available tissue culture growth media. The cells are incubated with an activation agent consisting of beads coated with antibodies to CD3/CD28. On about day 3, cells and beads are separated from the culture media and the cells and beads are resuspended in additional growth media as needed. To harvest the cells, they are resuspended in centrifuge tubes and pelleted, after which the supernatant can be drawn off with a pipet and stored for later use.

As used herein, the term "supernatant" refers to the liquid drawn off the cultured cells, in the manner described above. "Lymphocyte conditioned medium" and "supernatant" are used herein interchangeably, and refer to the liquid drawn off the cultured cells. Studies have been carried out to characterize the supernatant, and it has been found to contain molecules having an average molecular weights of less than about 100,000 daltons.

Administration is by known methods used for vaccination, and suitable delivery methods include, but are not limited to, intramuscular, intercutaneous and subcutaneous injection. Typically, about 10 μg to about 500 μg are administered in combination with the antigen. Administration can be weekly, biweekly, monthly or yearly, depending on the antigen and the level of immune response desired. Enhancement of the immune response can be observed, for example, by conducting standard assays known in the art that assess cellular immunity (such as T cell proliferation) and measure antibody titres post immunization.

The present invention is suitable for use with a large variety of vaccines, including, but not limited to, measles, mumps, rubella, influenza, haemophilus influenzae type B vaccines, diphtheria, tetanus, pertussis, pneumococcal polysaccharide vaccines, meningococcal polysaccharide vaccines, staphylococcus aureus vaccines, respiratory syncytial virus, streptococcus, parainfluenza mycoplasma pneumoniae, mycobacterium leprae, nocardia, legionella, pseudomonas, cholera vaccines, typhoid fever, poliovirus, hepatitis A vaccine, rotavirus, escherichia coli, shigella, hepatitis E, listeria, giardia lamblia, toxocariasis, trichuriasis, ascariasis, amebiasis, cysticercosis, hepatitis b recombinant and plasma-derived vaccines, HIV-1 and HIV-2; HTLVI and HTLV-II, Epstein-Barr, hepatitis C, herpes B, human papillomavirus, herpes simplex type 1 and 2, chlamydia, gonorrhea, treponema (syphilis), anthrax, rabies, schistosomiasis, plague, yellow fever vaccines, japanese encephalitis and tick-borne encephalitis vaccines, malaria, leishmaniasis, lyme disease, lymphatic filariasis and onchocerciasis, trypanosomiasis and chagas' disease, rickettsia and typhus fevers, dengue fever, adenovirus vaccines, varicella zoster vaccines, cytomegalovirus, coronaviruses and rhinioviruses, streptobacillus, allergy peptide, infectious disease peptide vaccine, cancer peptide vaccine, autoimmune peptide vaccine, and cancer vaccines utilizing antigen, peptide, DNA fragments and/or any other molecular species on the surface or within the cancer cell.

EXAMPLES

The following examples are intended to illustrate the invention and should not be construed as limiting the invention in any way. Experiments were carried out using the following materials and methods:

Cells

Human peripheral blood mononuclear cells (PBMC) used for preparation of the conditioned media were separated from leukapheresis products of normal healthy donors by density gradient centrifugation in Lymphocyte Separation Medium (ICN Biomedicals Inc., Aurora, Ohio). The cells were viably frozen in RPMI-1640 (Invitrogen Corp., Grand Island, N.Y.) containing 20% human AB serum (Gemini Bio-Products, Woodland, Calif.) and 10% DMSO (Sigma, St. Louis, Mo.) using an automated cell freezer (Gordinier Electronics, Roseville, Mich.) and stored in the vapor phase of liquid nitrogen until used. Monocytes were isolated from PBMC by countercurrent centrifugal elutriation and were used immediately or viably frozen in fetal bovine serum (Summit Biotechnology) containing 10% DMSO and 5% glucose (Sigma) for later use.

Preparation of LCM

Cryopreserved PBMC were thawed in RPMI-1640 supplemented with 20% human AB serum (hAB), washed twice with RPMI-1640 containing 10% hAB. Cells were resuspended in cRPMI [RPMI-1640 supplemented with 10% hAB, 2 mM L-glutamine (Invitrogen), 1% Penicillin Streptomycin Solution (Invitrogen), 20 mM Hepes Buffer (Invitrogen)] or X-Vivo 15 (BioWhittaker, Walkersville, Md.) supplemented with 2 mM L-glutamine, 1% Penicillin Streptomycin Solution, 20 mM Hepes Buffer. CD3/CD28 Dynabeads (Dynal, Lake Success, N.Y.) were added to the cells at 75:1 of beads for every $1 \times 10^6$ PBMC and the cultures were incubated for 3 days at 37° C. in 5% $CO_2$. Subsequently, cell-free supernatants were collected and stored at 2-8° C. prior to use. LCM was used at a 1:1 dilution in cRPMI.

Culturing Elutriated Monocytes

Elutriated monocytes were washed with cRPMI, resuspended in equal volumes of LCM and cRPMI at a concentration of $5 \times 10^5$ cells/ml, and cultured in 24 well plates (Denville Scientific Inc., Metuchen, N.J.) at 37° C. in 5% $CO_2$ for 5-6 days. Alternatively, monocytes were cultured in cRPMI containing 750 U/ml GM-CSF (R&D Systems, Minneapolis, Minn.) and 720 U/ml IL-4 (R&D Systems) for 3-4 days followed by addition of the conditioned media or a combination of cytokines [10 ng/ml IL-1β, 10 ng/ml TNFα, 0.91 ng/ml IL-6 (R&D Systems), 1:g/ml $PGE_2$ (Sigma)] (Maturation Cocktail) for an additional 48 hours. The Maturation Cocktail served as a positive control and monocytes cultured in cRPMI only were used as a negative control.

Flow Cytometry

Cells were washed once in cRPMT, resuspended in 1×PBS (Invitrogen) containing 5% hAB, and incubated for 15 minutes at room temperature (22-25° C.) in order to block Fc receptors. Cells were then washed, resuspended in wash buffer (1×PBS with 1% hAB and 0.1% $NaN_3$), and labeled with fluorochrome-conjugated antibodies (BD BioSciences, San Diego, Calif.) against CD14, CD11c, CD40, CD83, CD80, CD86, and appropriate isotype control antibodies. After 30 minutes at 4° C., the cells were washed with buffer and fixed in 1×PBS with 1% paraformaldehyde. Flow cytometric data were acquired using a FACScan flow cytometer and analyzed with CellQuest software (Becton Dickinson, SanJose, Calif.). Gates were set according to isotype control samples.

Cytokine and Chemokine Analysis

Cytokines and chemokines in LCM were quantified using commercially available enzyme-linked immunosorbent assays (ELISAs; R & D Systems, Minneapolis, Minn.) according to manufacturer's guidelines. The concentration of $PGE_2$ was also measured by ELISA (Cayman Chemical Co., Ann Arbor, Mich.). All determinations were made in duplicate.

Allogeneic MLR

Dendritic cells were harvested from cultures, washed twice in cRPMI, and plated into 96-well U-bottom culture plates (Denville Scientific, Inc.) at $10^4$, $10^3$, and $10^2$ cells per well. Allogeneic responder PBMC were added to each well at $1 \times 10^5$ cell/well in a total volume of 200:1. All conditions were plated in triplicate. The cells were incubated for 3 days at 37° C. in 5% $CO_2$, pulsed with 1.0:Ci tritiated thymidine (Perkin Elmer, Boston, Mass.) for 16 hours, and harvested using an automated multi-well harvester (Tomtec, Orange, Conn.). The amount of tritiated thymidine incorporated into the responder cells was measured using the MicroBeta TriLux liquid scintillation counter (Wallac, Turku, Finland).

Antigen Stimulation Assay

Unprimed normal human PBMC ($1 \times 10^5$/100:1 cRPMI) were plated into 96-well U-bottom culture plates to which 100:1 of LCM or 100:1 cRPMI with or without 10:g/ml tetanus toxoid (Accurate Chemical and Scientific Corp., Westbury, N.Y.) was added. PBMC cultured in cRPMI with 10:g/ml ConcanavalinA (Sigma, St. Louis, Mo.) served as a positive control. All conditions were plated in triplicate, cultured at 37° C. in 5% $CO_2$ for 3 and 5 days, pulsed with 1.0:Ci tritiated thymidine for 16 hours, and harvested using an automated multi-well harvester. The amount of tritiated thymidine incorporated into the responder cells was measured using the MicroBeta TriLux liquid scintillation counter.

LCMD Differentiates Monocytes to Dc in the Absence of Additional Cytokines

Figure 1A:
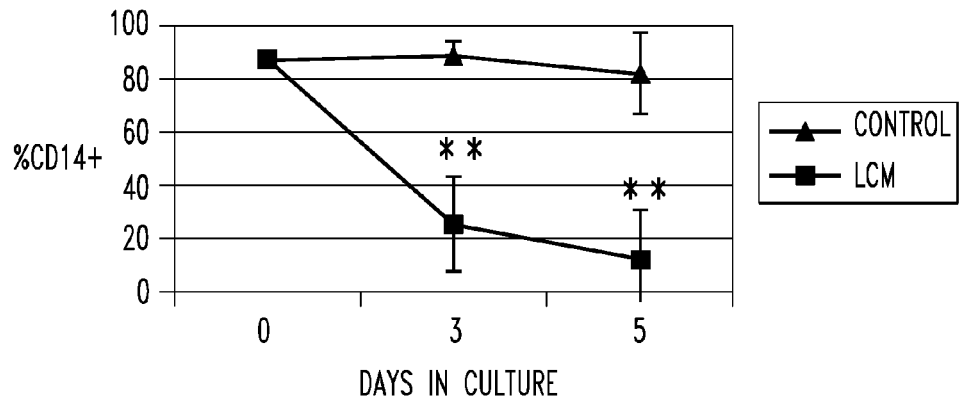
FIGS. 1A-1E: LCM induces a DC-like phenotype in monocytes cultured with LCM only. Expression of CD14 (FIG. 1A), HLA-DR (FIG. 1B), CD40 (FIG. 1C), CD80 (FIG. 1D), and CD86 (FIG. 1E) was analyzed at different time points.
Figure 1B:
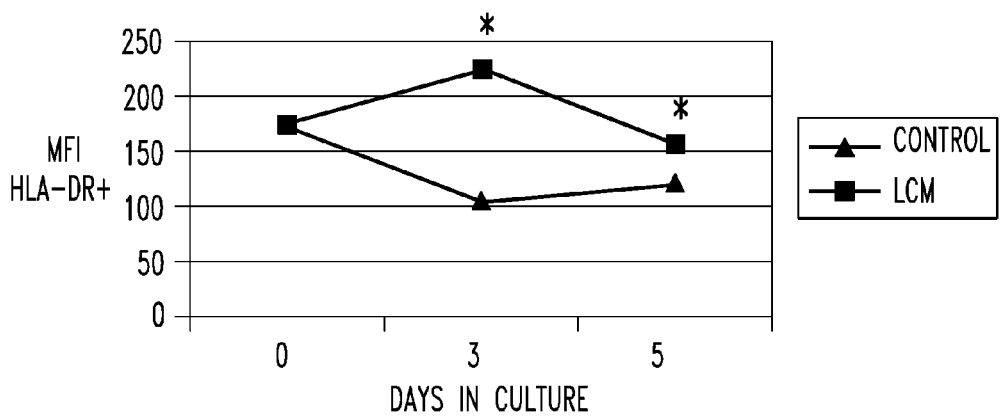
Figure 1C:
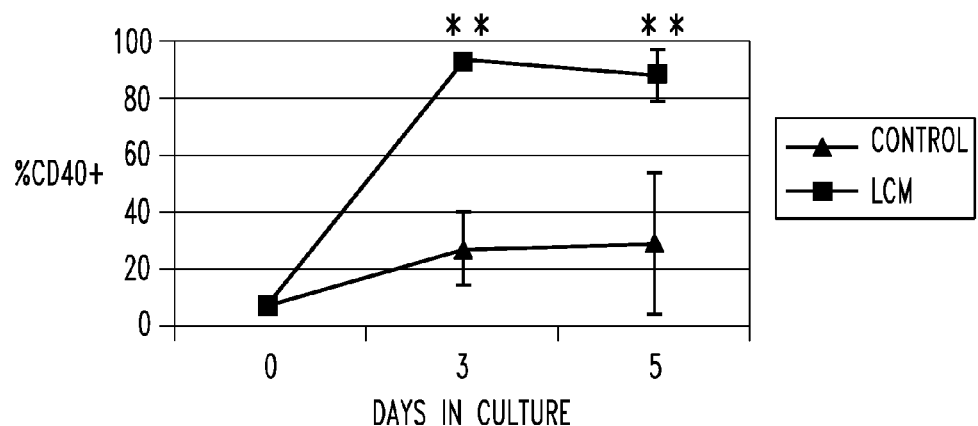
Figure 1D:
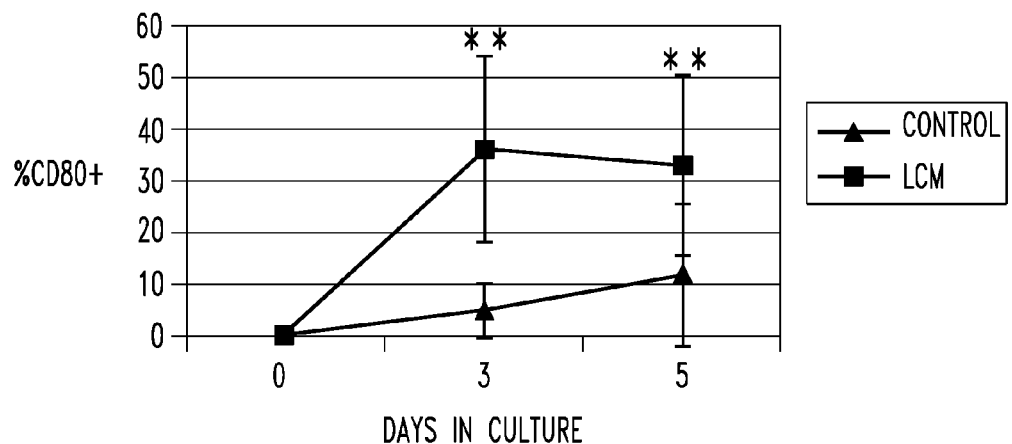
Figure 1E:
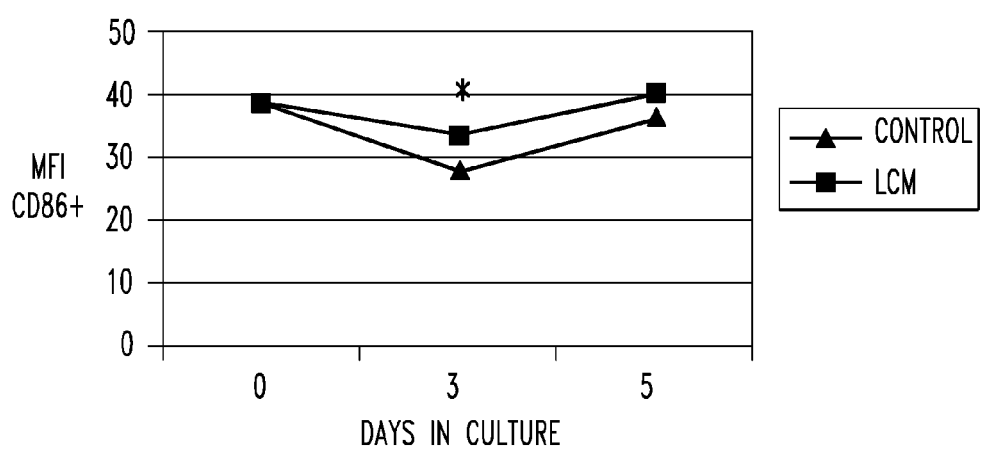

In an effort to generate a highly effective cytokine cocktail for the generation and maturation of large numbers of human DC from their in vitro precursors, we produced culture supernatants from anti-CD3/anti-CD28 stimulated PBMC (LCM) as described in Material and Methods and investigated their effect on highly purified human monocytes obtained from PBMC by counter flow centrifugation. Monocytes were cultured in LCM in the absence of GM-CSF and IL-4 and the expression of cell surface markers that characterize differentiated and matured DC was examined by flow cytometry. Prior to culture, monocytes constitutively expressed CD11c, as well as CD14 and HLA-DR. Culture in LCM resulted in a significant decrease of the percent of cells expressing CD14 by day 3, and by days only a few cells expressing this marker remained (FIG. 1A). The MFIs of HLA-DR (FIG. 1B), CD40 (FIG. 1C), CD80 (FIG. 1D) and CD86 (FIG. 1E) were consistently upregulated on cells cultured in LCM as compared to cells cultured on medium alone. In 4 out of 9 experiments, a small percentage of CD83+ DC was observed; however, these results were not significant. Taken together, LCM differentiates monocytes into phenotypically immature DC, a stage of development that is optimal for antigen acquisition.

LCM Matures Monocytes Cultured in GM-CSF/IL-4

The ability of LCM to mature immature DC that were generated in vitro from monocytes in the presence of GM-CSF and IL-4 was assessed. Monocytes obtained from PBMC by elutriation were cultured for 3-4 days in media containing GM-CSF and IL-4 followed by addition of LCM or a standard Maturation Cocktail containing IL-1β, TNFα, IL-6 and $PGE_2$ (see Materials and Methods). Flow cytometry was performed 48 hours later. As shown in FIG. 2 and Table 1, both LCM and Maturation Cocktail induced the expression of HLA-DR, costimulatory molecules and CD83, generally accepted signatures for mature DC. These results indicate that LCM can facilitate the final maturation of immature monocyte-derived DC. The DC maturation activity of LCM obtained from a total of four different donors was very consistent (Data not shown).

TABLE 1

Surface Marker Expression on Monocytes Cultured in GM-CSF and 1L4 With or Without LCM

| Marker | MFI | | | Percent | | |
|---|---|---|---|---|---|---|
| | (+) LCM | (−) LCM | p Value | (+) LCM | (−) LCM | p Value |
| CD40 | 110 ± 43 | 37 ± 16 | 0.003 | 95 ± 3 | 5 ± 26 | 0.003 |
| CD83 | 18 ± 12 | 9 ± 5 | 0.026 | 17 ± 11 | 5 ± 2 | 0.014 |
| CD80 | 55 ± 37 | 13 ± 7 | 0.007 | 56 ± 21 | 15 ± 6 | 0.0003 |
| CD86 | 182 ± 116 | 179 ± 108 | NS | 90 ± 7 | 86 ± 19 | NS |

Table 1: Statistical evaluation of ME1 and percent expression of CD40, CD83, CD80, and CD86 on monocytes cultured with GM-CSF/IL-4 with (+LCM) or without (−LCM) addition of LCM for the last 48 hours. Data is expressed as means±SEM from 8 experiments and statistical significance was determined by the paired two-tailed Student t test.

Monocytes in PBMC Express Accessory Molecules when Cultured with LCM

Figure 3A:
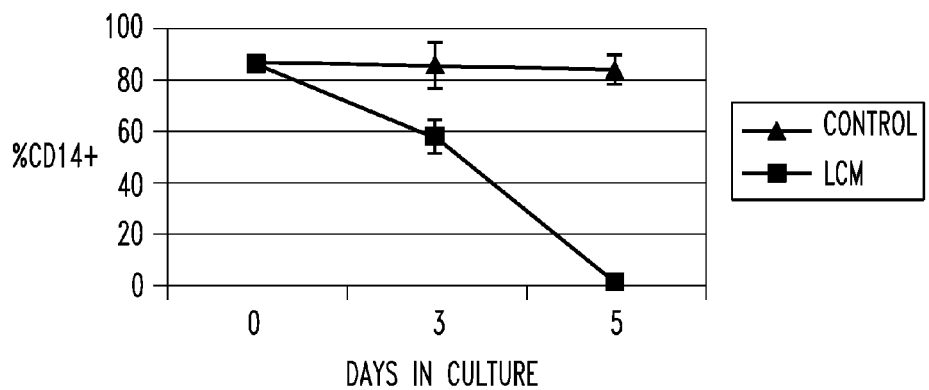
Figure 3B:
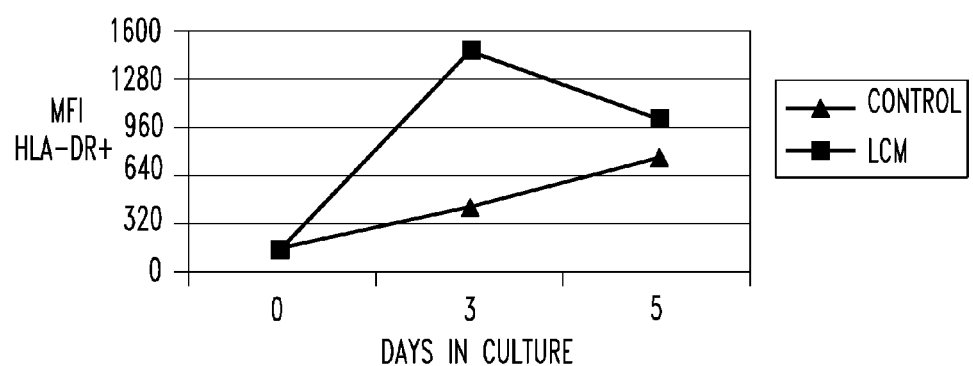
Figure 3C:
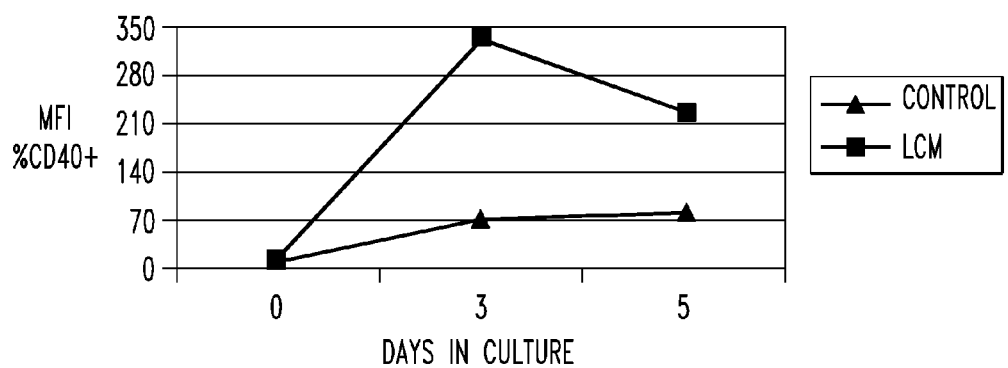
Figure 3D:
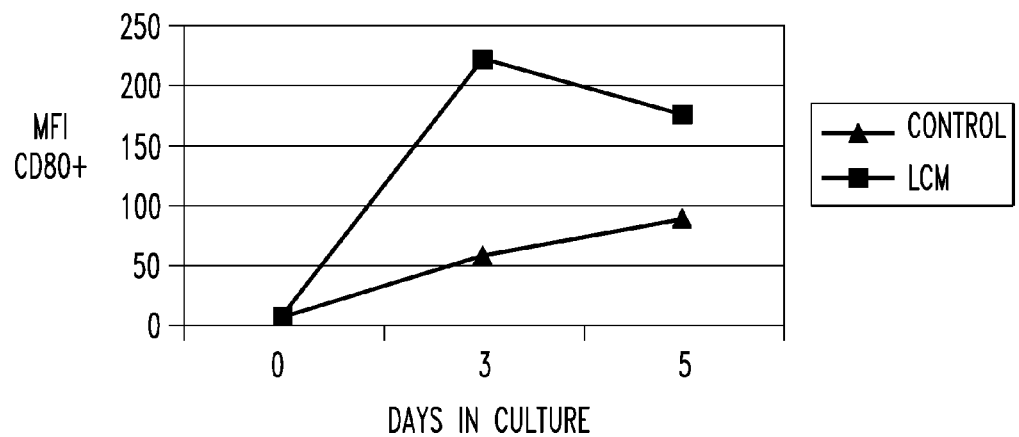
Figure 3E:

To investigate the effect of LCM on the distribution and phenotype of various cell populations contained in peripheral blood in vivo, whole PBMC were cultured in LCM for 3 or 5 days. No differences in the percentages of CD3+, CD4+−, CD8+, CD56+, and CD19+ cells were found at these two time points (data not shown). Also, the percentages of CD3+ cells co-expressing CD25, a marker for activation, did not increase over the 5-day period of culture (data not shown). However, the expression of CD14 on monocytes, identified by their expression of CD11c, declined at day 3 and was almost completely downregulated by day 5 (FIG. 3A). By contrast, the expression of HLA-DR, CD40, CD80 and CD86 on CD11c+ cells was upregulated (FIG. 3). Thus, LCM differentiates highly purified monocytes as well as monocytes within whole PBMC into cells with a DC-like phenotype.

Cytokine and Chemokine Concentrations in LCM

Cytokine and chemokine concentrations in LCM (Table 2) were determined by standard ELISA methods and compared with concentrations of cytokines commonly used for the generation or maturation of DC (Table 3). A whole battery of soluble mediators was identified, including GMCSF and IL-4, inflammatory cytokines (IL-1β, IL-6, $PGE_2$, TNFα, IFN(γ) chemokines (MCP-1, MIP1, RANTES), and sCD40L (Table 2). Strikingly, the concentrations of GM-CSF and IL-4 in LCM were significantly lower than concentrations of the two cytokines used in standard protocols for the generation of immature DC from monocytes (Table 3). One of the actions of IL4 on monocytes during the in-vitro differentiation to immature DC is the down regulation of CD14 expression. The low level of IL-4 in LCM may account for the relatively slow downregulation of CD14 on monocytes cultured in LCM (FIG. 1A, 3A). There were also lower concentrations of inflammatory cytokines in LCM compared to Maturation Cocktail, even though both maturation agents had comparable effects on immature DCs.

TABLE 2

Quantification of Cytokines and Chemokines in Contained in LCM

| Cytokine or Chemokine | Quantity (ng/ml) |
| --- | --- |
| GM-CSF | 23.98 |
| IFNα | 0.00 |
| IFNγ | 31.44 |
| IL-1β | 0.07 |
| IL-2 | 5.91 |
| IL-3 | 1.04 |
| IL-4 | 0.28 |
| IL-6 | 2.17 |
| IL-8 | 47.97 |
| IL-b | 0.66 |
| IL-12 | 0.01 |
| IL-15 | 0.00 |
| MCP-1 | 110.04 |
| M-CSF | 8.69 |
| MIP-1α | 127.20 |
| MIP-1β | 157.89 |
| $PGE_2$ | 1.54 |
| RANTES | 20.64 |
| sCD40L | 1.27 |
| SDF-1α | 0.00 |
| TGFβ | 0.00 |
| TNFα | 6.43 |

Table 2: Average cytokine or chemokine concentration in four different LCM preparations as determined by ELISA

TABLE 3

Quantities of Cytokines in LCM, GM-CSF/IL4 Medium, and Maturation Cocktail
Quantity of Cytokine Added to Cell Cultures (ng/ml)

| | LCM* | GM-CSF/IL4 Medium |
| --- | --- | --- |
| GM-CSF | 11.99 | 50.00 |
| IL-4 | 0.14 | 20.16 |
| | | Maturation Cocktail |
| IL-1β | 0.035 | 10.00 |
| IL-6 | 1.085 | 9.09 |
| $PGE_2$ | 0.770 | 1000.00 |
| TNFα | 3.215 | 10.00 |

Table 3: The quantifies of GM-CSF and IL4 contained in LCM are compared with those used in standard protocols for the generation of monocyte-derived DCs, as are the concentrations of selected proinflammatory cytokines in LCM and Maturation Cocktail. * Note that the cytokine concentrations for LCM given in this table are half of those in Table 2: because LCM is added to cells at a 1:1 dilution in cRPMI.

Monocytes Cultured in LCM Stimulate Allogeneic PBMC

A functional characteristic of monocyte-derived DC is their capacity to effectively induce allogeneic responses in vitro. The allogeneic response of PBMC to monocytes that have been cultured for five days in the absence or in the presence of LCM, or that were cultured in media containing GM-CSF/IL-4 followed by addition of cRPMI or LCM was determined. As shown in FIG. 4, the stimulation index (SI) generated by monocytes cultured in LCM alone was approximately 3 times that induced by monocytes that have been cultured in cRPMI alone. However, the SI was highest with monocytes that have been cultured in GM-CSF/IL-4 and matured with LCM. These results demonstrate that LCM renders monocytes and immature DC into more effective antigen presenting cells.

LCM Enhances PBMC Response to Tetanus Toxoid

In addition the proliferative responses of PBMC to the recall antigen tetanus toxoid (TT) were tested, again in the presence or absence of LCM (FIG. 5A). In the absence of LCM and other cytokines, PBMC showed low levels of response to TT; however with the addition of LCM the response to TT significantly increased at day 6 (FIG. 5a). It is important to point out that LCM alone induced DNA synthesis in PBMC even in the absence of specific antigen; nevertheless the response to the specific antigen was significantly augmented. To determine if the observed response to TT was mediated by monocytes, the experiments were repeated using PBMC that had been depleted of CD 14+ cells with immunomagnetic beads. As illustrated in FIG. 5B, there was no response to TT with or without the addition of LCM. The higher SI in the experiments where monocytes were removed (FIG. 5B) can be accounted for by the relative increase in the numbers of other cell types, particularly the CD3+ cells (data not shown). These results clearly indicate that LCM enhances the capacity of the PBMC to respond to TT' sand that the response is mediated by monocytes.

The above findings indicate that LCM rendered highly purified monocytes and monocytes in whole PBMC into a DC-like phenotype. In addition, immature monocyte-derived DC developed a mature DC phenotype after culture in LCM. Functionally, these LCM-derived DC showed an increased capacity to stimulate allogeneic PBMC compared to their monocyte precursors and significantly augmented the response to TT. The observed effects of LCM can be accounted for by the battery of proinflammatory cytokines and chemokines identified in the conditioned medium.

Whereas particular embodiments of this invention have been described above for purposes of illustration, it will be evident to those skilled in the art that numerous variations of the details of the present invention may be made without departing from the invention as defined in the appending claims.

REFERENCES

1. Banchereau J, Briere F, Caux C, et al. Immunobiology of dendritic cells. Annu Rev Immunol JID-8309206 2000; 18:767-811.
2. Banchereau J, Steinman R M. Dendritic cells and the control of immunity. Nature JID 0410462 1998; 392:245-252.
3. Steinman R M. The dendritic cell system and its role in immunogenicity. Annu Rev Immunol JID-8309206 1991; 9:271-296.
4. Hart D N, McKenzie J L. Interstitial dendritic cells. Int Rev Immunol JID-8712260 1990; 6:127-138.
5. Liu Y J. Dendritic cell subsets and lineages, and their functions in innate and adaptive immunity. Cell JID-0413066 2001; 106:259-262.
6. Liu Y J, Kanzler H, Soumelis V, Gilliet M. Dendritic cell lineage, plasticity and cross-regulation. Nat Immunol JID-100941354 2001; 2:585-589.
7. Palucka K, Banchereau J. How dendritic cells and microbes interact to elicit or subvert protective immune responses. Curr Opin Immunol JID-8900118 2002; 14:420-431.
8. Sallusto F, Cella M, Danieli C, Lanzavecchia A. Dendritic cells use macropinocytosis and the mannose receptor to concentrate macromolecules in the major histocompatibility complex class II compartment: downregulation by cytokines and bacterial products. J Exp Med JID-2985109R 1995; 182:389-400.
9. Bottomly K. T cells and dendritic cells get intimate. Science JID-0404511 1999; 283:1124-1125.
10. Reid S D, Penna G, Adorini L. The control of T cell responses by dendritic cell subsets. Curr Opin Immunol JID-8900118 2000; 12:114-121.
11. O'Doherty U, Peng M, Gezelter S, et al. Human blood contains two subsets of dendritic cells, one immunologically mature and the other immature Immunology JID-0374672 1994; 82:487-493.
12. O'Doherty U, Steinman R M, Peng M, et al. Dendritic cells freshly isolated from human blood express CD4 and mature into typical immunostimulatory dendritic cells after culture in monocyte-conditioned medium. J Exp Med JID-2985109R 1993; 178:1067-1076.
13. Randolph G J, Inaba K, Robbiani D F, Steinman R M, Muller W A. Differentiation of phagocytic monocytes into lymph node dendritic cells in vivo Immunity JID-9432918 1999; 11:753-761.
14. Robinson S P, Patterson S, English N, Davies D, Knight S C, Reid C D. Human peripheral blood contains two distinct lineages of dendritic cells. Eur J Immunol JID-1273201 1999; 29:2769-2778.
15. Zhou L J, Tedder T F. CD14+ blood monocytes can differentiate into functionally mature CD83+ dendritic cells. Proc Nail Acad Sci USA JID-7505876 1996; 93:2588-2592.
16. Dauer M, Obermaier B, Herten J, et al. Mature dendritic cells derived from human monocytes within 48 hours: a novel strategy for dendritic cell differentiation from blood precursors. J Immunol JID-2985117R 2003; 170:4069-4076.
17. Kiertscher S M, Roth M D. Human CDI4+ leukocytes acquire the phenotype and function of antigen-presenting dendritic cells when cultured in GM-CSF and IL-4. J Leukoc Biol JID-8405628 1996; 59:208-218.
18. Pickl W F, Majdic O, Kohl P, et al. Molecular and functional characteristics of dendritic cells generated from highly purified CD 14+ peripheral blood monocytes. J Immunol JID-2985117R 1996; 157:3850-3859.
19. Sallusto F, Lanzavecchia A. Efficient presentation of soluble antigen by cultured human dendritic cells is maintained by granulocyte/macrophage colony-stimulating factor plus interleukin 4 and downregulated by tumor necrosis factor alpha. J Exp Med JID-2985109R 1994; 179:1109-1118.
20. Cella M, Salio M, Sakakibara Y, Langen H, Julkunen I, Lanzavecchia A. Maturation, activation, and protection of dendritic cells induced by double-stranded RNA. J Exp Med JID-2985109R 1999; 189:821-829.
21. Chomarat P, Dantin C, Bennett L, Banchereau J, Palucka A K. TNF skews monocyte differentiation from macrophages to dendritic cells J Immunol JID-2985117R 2003; 171:2262-2269.
22. Jonuleit H, Kuhn U, Muller G, et al. Pro-inflammatory cytokines and prostaglandins induce maturation of potent immunostimulatory dendritic cells under fetal calf serum-free conditions. Eur J Immunol JID-1273201 1997; 27:3135-3142.
23. Verdijk R M, Mutis T, Esendam B, et al. Polyriboinosinic polyribocytidylic acid (poly(I:C)) induces stable maturation of functionally active human dendritic cells. J Immunol JID-2985117R 1999; 163:57-61.
24. Zou G M, Tam Y K. Cytokines in the generation and maturation of dendritic cells: recent advances. Eur Cytokine Netw JID-9100879 2002; 13:186-199.
25. Kato K, Takaue Y, Wakasugi H. T-cell-conditioned medium efficiently induces the maturation and function of human dendritic cells. J Leukoc Biol JID-8405628 2001; 70:941-949.
26. Reddy A, Sapp M, Feldman M, Subklewe M, Bhardwaj N. A monocyte conditioned medium is more effective than defined cytokines in mediating the terminal maturation of human dendritic cells. Blood JID-7603509 1997; 90:3640-3646.
27. Guermonprez P, Valladeau J, Zitvogel L, Thery C, Amigorena S. Antigen presentation and T cell stimulation by dendritic cells. Annu Rev Immunol JID-8309206 1903; 20:621-667.
28. Inaba K, Metlay J P, Crowley M T, Steinman R M. Dendritic cells pulsed with protein antigens in vitro can prime antigen-specific, MHC-restricted T cells in situ. J Exp Med JID-2985109R 1990; 172:631-640.
29. Toujas L, Delcros J G, Diez E, et al. Human monocyte-derived macrophages and dendritic cells are comparably effective in vitro in presenting HLA class I-restricted exogenous peptides. Immunology JID-0374672 1997; 91:635-642.
30. Weissman D, Ni H, Scales D, et al. HIV gag mRNA transfection of dendritic cells (DC) delivers encoded antigen to MHC class I and II molecules, causes DC maturation, and induces a potent human in vitro primary immune response. J Immunol JID-2985117R 2000; 165:4710-4717.

31. Gallucci S, Lolkema M, Matzinger P. Natural adjuvants: endogenous activators of dendritic cells. Nat Med JID-9502015 1999; 5:1249-1255.
32. Dieu M C, Vanbervliet B, Vicari A, et al. Selective recruitment of immature and mature dendritic cells by distinct chemokines expressed in different anatomic sites. J Exp Med JID-2985109R 1998; 188:373-386.
33. Krug A, Rothenfusser S, Selinger S, et al. CpG-A oligonucleotides induce a monocyte-derived dendritic cell-like phenotype that preferentially activates CD8 T cells. J Immunol JID-2985117R 2003; 170:3468-3477.
34. Luft T, Jefford M, Luetjens P. et al. Functionally distinct dendritic cell (DC) populations induced by physiologic stimuli: prostaglandin E(2) regulates the migratory capacity of specific DC subsets. Blood JID-7603509 2002; 100: 1362-1372.
35. Sallusto F, Palermo B, Lenig D, et al. Distinct patterns and kinetics of chemokine production regulate dendritic cell function. Eur J Immunol JID-1273201 1999; 29:1617-1625.
36. Thumer B, Roder C, Dieckmann D, et al. Generation of large numbers of fully mature and stable dendritic cells from leukapheresis products for clinical application. J Immunol Methods JID-1305440 1999; 223:1-15.
37. Hartmann G, Weiner G J, Krieg A M. CpG DNA: a potent signal for growth, activation, and maturation of human dendritic cells. Proc Natl Acad Sci USA JID-7505876 1999; 96:9305-9310.
38. Kadowaki N, Liu Y J. Natural type I interferon-producing cells as a link between innate and adaptive immunity. Hum Immunol JID-8010936 2002; 63:1126-1132.
39. Rothenfusser S, Tuma E, Endres S, Hartmann G. Plasmacytoid dendritic cells: the key to CpG(1). Hum Immunol JID-8010936 2002; 63:1111-1119.
40. O'Garra A. Cytokines induce the development of functionally heterogeneous T helper cell subsets. Immunity JID-9432918 1998; 8:275-283.
41. Pulendran B, Smith J L, Caspary G, et al. Distinct dendritic cell subsets differentially regulate the class of immune response in vivo. Proc Nail Acad Sci USA JID-7505876 1999; 96: 1036-1041.
42. Sallusto F, Schaerli P, Loetscher P, et al. Rapid and coordinated switch in chemokine receptor expression during dendritic cell maturation. Eur J Immunol JID-1273201 1998; 28:2760-2769.
43. Appay V, Rowland-Jones S L. RANTES: a versatile and controversial chemokine. Trends Immunol JID-100966032 2001; 22:83-87.

What is claimed is:

1. A composition for enhancing an immune response to an antigen in a mammal, comprising an antigen in combination with lymphocyte conditioned medium, said lymphocyte conditioned medium is the supernatant derived from cultures of peripheral blood mononuclear cells activated with anti-CD3- and anti-CD28-coated beads, wherein said composition when administered to a mammal facilitates and enhances dendritic cell maturation and antigen-presenting cell function which results in enhanced immunologic responses to said antigen in the mammal.

2. The composition of claim 1, wherein said antigen is HIV-1 or HIV-2.

3. The composition of claim 1, wherein said antigen is hepatitis-B.

4. The composition of claim 1, wherein said antigen is tetanus toxoid.

5. The composition of claim 1, wherein said antigen is prostate-specific antigen.

6. The composition of claim 1, wherein said antigen is hepatitis-A.

7. The composition of claim 1, wherein said antigen is diptheria.

8. The composition of claim 1, wherein said antigen is selected from the group consisting of viruses, bacteria, fungi, proteins, peptides, DNA fragments, other molecular species found on surfaces or within cancer cells and combinations thereof."

9. The composition of claim 1, wherein the dosage administered to the mammal is about 10 µg to about 500 µg.

10. The composition of claim 1, wherein route of administration is selected from the group consisting of intracutaneous, subcutaneous and intramuscular injection and combinations thereof.

11. The composition of claim 1, wherein timing of administration is selected from the group consisting of weekly, biweekly, monthly, yearly and combinations thereof.

12. A composition for enhancing an immune response to an antigen in a mammal, comprising a vaccine comprised of an antigen and lymphocyte conditioned medium, said lymphocyte conditioned medium is the supernatant derived from cultures of peripheral blood mononuclear cells activated with anti-CD3- and anti-CD28-coated beads, wherein said composition when administered to a mammal facilitates and enhances dendritic cell maturation and antigen-presenting cell function which results in enhanced immunologic responses to said antigen in the mammal.

* * * * *